United States Patent [19]
Wacks

[11] Patent Number: 5,354,287
[45] Date of Patent: Oct. 11, 1994

[54] INJECTOR FOR DELIVERING FLUID TO INTERNAL TARGET TISSUE

[75] Inventor: Jonathan L. Wacks, Forest Hills, N.Y.

[73] Assignee: Senetek PLC, St. Louis, Mo.

[21] Appl. No.: 641,752

[22] Filed: Jan. 16, 1991

[51] Int. Cl.$^5$ ............................................. A61M 5/00
[52] U.S. Cl. ................................. 604/232; 604/197; 604/201; 604/240; 604/403; 604/413; 604/414; 604/415; 141/329; 141/383; 141/386; 128/DIG. 1
[58] Field of Search ............... 604/232, 234, 194, 195, 604/196, 202, 200, 213, 110, 156, 201, 197, 121, 123–125, 130, 137–139, 403, 411–416, 205, 206, 233, 235, 236, 237, 239, 240, 144, 146, 171; 128/DIG. 1; 222/326, 386; 141/27, 329, 330, 383, 385, 386

[56] References Cited

U.S. PATENT DOCUMENTS

| | | |
|---|---|---|
| 2,345,301 | 3/1944 | Smith . |
| 2,701,566 | 2/1955 | Krug . |
| 2,832,339 | 4/1958 | Sarnoff et al. . |
| 2,876,770 | 3/1959 | White . |
| 3,066,670 | 12/1962 | Stauffer . |
| 3,136,313 | 6/1964 | Enstrom et al. . |
| 3,182,660 | 5/1965 | Weydanz et al. . |
| 3,395,704 | 8/1968 | Frey et al. . |
| 3,702,609 | 11/1972 | Steiner . |
| 3,742,948 | 7/1973 | Post et al. . |
| 3,820,542 | 6/1974 | Hurschman ............... 604/235 |
| 4,055,177 | 10/1977 | Cohen . |
| 4,108,177 | 8/1978 | Pistor . |
| 4,116,196 | 9/1978 | Kaplan et al. ............... 604/201 |
| 4,178,928 | 12/1979 | Tischlinger ............... 604/202 |
| 4,316,463 | 2/1982 | Schmitz et al. ............... 604/194 |
| 4,328,802 | 5/1982 | Curley et al. . |
| 4,394,863 | 7/1983 | Bartner ............... 604/90 |
| 4,499,148 | 2/1985 | Goodale et al. . |
| 4,553,962 | 11/1985 | Brunet ............... 604/232 |
| 4,617,016 | 10/1986 | Blomberg . |
| 4,664,653 | 5/1987 | Sagstetter et al. ............... 604/194 |
| 4,689,042 | 8/1987 | Sarnoff et al. ............... 604/191 |
| 4,693,706 | 9/1987 | Ennis, III ............... 604/87 |
| 4,719,825 | 1/1988 | LaHaye et al. . |
| 4,755,169 | 7/1988 | Sarnoff et al. ............... 604/89 |
| 4,767,413 | 8/1988 | Haber et al. ............... 604/232 |
| 4,781,700 | 11/1988 | Vicario ............... 604/234 |
| 4,808,184 | 2/1989 | Tepic ............... 604/56 |
| 4,834,717 | 5/1989 | Haber et al. ............... 604/232 |
| 4,931,040 | 6/1990 | Haber et al. . |
| 4,936,169 | 6/1990 | Sams ............... 604/232 |
| 4,936,833 | 6/1990 | Sams ............... 604/232 |
| 4,950,246 | 8/1990 | Muller . |
| 4,955,869 | 9/1990 | Bin . |
| 4,968,299 | 11/1990 | Ahlstrand et al. ............... 604/232 |
| 4,968,302 | 11/1990 | Schluter et al. ............... 604/135 |
| 4,983,164 | 1/1991 | Hook et al. . |
| 5,092,842 | 3/1992 | Bechtold et al. ............... 604/232 |
| 5,094,148 | 3/1993 | Haber et al. ............... 604/218 |
| 5,098,382 | 3/1992 | Haber et al. ............... 604/232 |
| 5,102,393 | 4/1992 | Sarnoff et al. ............... 604/136 |
| 5,112,317 | 5/1992 | Michel ............... 604/232 |
| 5,114,406 | 5/1992 | Gabriel et al. ............... 604/232 |

OTHER PUBLICATIONS

Variject–2–Kammerspritze, Variject two-compartment Syringe.

*Primary Examiner*—C. Fred Rosenbaum
*Assistant Examiner*—Ron Stright, Jr.
*Attorney, Agent, or Firm*—Fitch, Even, Tabin & Flannery

[57] ABSTRACT

An injector for delivering fluid to a preselected internal target tissue while avoiding fluid exposure to surface tissue. A needle housing assembly is concealed within a cartridge having a puncturable end cap and an ampule is also disposed within the cartridge separate from the needle housing assembly. The cartridge has a cylindrical bore which widens at one end such that the needle housing assembly which has walls while located within the narrower portion of the cylindrical bore prevents the ampule from being punctured by a hollow injection needle supported by the needle housing assembly. When the ampule is propelled toward the needle housing assembly with a plunger, the needle housing assembly enters the widened portion of the cylindrical bore, allowing its walls to be separated such that the hollow injection needle extends into the ampule allowing the fluid to be delivered from the ampule through the hollow injection needle to the internal target tissue.

14 Claims, 4 Drawing Sheets

INJECTOR FOR DELIVERING FLUID TO INTERNAL TARGET TISSUE

BACKGROUND OF THE INVENTION

The present invention relates to an injection/aspiration device and a cartridge vial for use therewith for medical and research purposes and more particularly to a device designed for injecting medicines and other fluids into human beings and other subjects using a hollow injection needle. Both the injection/aspiration and cartridge vial components of the invention are also configured to aspirate blood and/or other fluids.

In the conventional medical procedure for injecting medicines or for aspirating blood or fluids, a syringe with a hollow injection/aspiration needle, such as a standard hypodermic needle, is used. Needles are repugnant to many patients, particularly those who must have regular injections of medicine or blood samples taken. Among these are elderly patients and people who must have daily injections of insulin or other drugs. Similarly, pediatric patients are particularly afraid of needles. Exposed or visible needles are undesirable because they create fear and apprehension in many subjects.

Another problem in the medical field is that of the communication of infectious diseases caused by used needles and syringes and fluids therefrom coming into contact with doctors, nurses, or other medical personnel. Needle tips often remain exposed after aspiration of a fluid or blood from a subject, or after injection of a medicine into a subject and medical personnel are sometimes accidentally pricked with such tips. This problem is particularly acute in situations where a syringe and needle have been contaminated with particularly virulent organisms such as the AIDS virus or the hepatitis virus. The risk of puncture with a contaminated needle point is of particular concern after an injection because a finger, hand or other part of the person administering the injection is typically in close physical proximity to the needle during its removal from the subject's tissues, during replacement of a needle or the needle cover or during removal of the needle from a syringe for disposal.

There is also danger of such exposures to personnel, such as maintenance people, other than medical personnel, when a used needle and/or syringe is laid aside or discarded with a needle tip still exposed. This danger continues even when a used needle and/or syringe are placed in a disposal container. For instance, it is a routine medical procedure to use a device which cuts off the tip of an exposed needle so that it may not be reused. However, this procedure still leaves exposed needle stubs and syringe parts which may be contaminated with infectious agents and with which persons may come into contact and be infected. Thus, it is not uncommon for discarded needle stubs to protrude through plastic garbage bags or other containers and present serious risk of a puncture wound to a person handling or otherwise coming into contact with the container. Similarly, even after used needles are removed from syringes and placed in sealed containers, the exposed syringes must also be placed in sealed containers to reduce the likelihood of infectious contact with personnel. Sanitary disposal of used needles and used syringes is an expensive and time consuming process and entails significant risk of exposure to infectious disease vectors.

A related problem is that of the dangers of exposing a needle to the atmosphere prior to its being used in giving an injection or withdrawing a body fluid. Not only is there danger of wounds to user personnel and patients from the exposed needle tip, but also there is the danger that the exposed needle will become contaminated by airborne or aerosol borne microbial and other contaminants and infect the patient eventually injected. This danger is particularly acute in hospitals and other medical treatment areas where strains of antibiotic-resistant microbes endemically contaminate the air and all exposed surfaces. Contact with non-sterile air is a certainty with conventional exposed needle syringe technology because, in this technology, needles are routinely exposed to the air or surfaces for some discrete amount of time during use. Also, in emergency use situations such as military combat, natural disasters, or industrial accidents, the unused needle may be left exposed to such contaminants by untrained, harried or inexperienced personnel.

Yet another common problem in conventional syringe/injection technology is that relating to improperly given injections. The differences in the rate which a needle must travel during insertion into and withdrawal from the subject's tissues and the rate at which a syringe piston must be operated in order to inject or aspirate fluid in a painless manner are substantial. The techniques of various medical personnel in using conventional syringes are varied. Techniques vary according to the position of the subject, how that portion of the subject's anatomy which is to be injected is held, and by the various individual techniques of medical personnel. This problem is particularly acute with respect to untrained or inexperienced personnel. When a needle is inserted too slowly, needless pain results. These problems are overwhelmingly due to the difficulty of operating a syringe and needle in a manner which appropriately varies the rates of needle insertion and withdrawal and the rates of fluid injection and aspiration.

An additional problem in the field is that of dosage management. For subjects who give themselves injections, either because they require regular doses of injected pharmaceuticals or because medical personnel are not available, it is critical to insure that dosages are correct. Diabetic subjects often find themselves in such situations, particularly diabetics who suffer from the related condition of blindness. Other blind people are similarly in need of a product which insures that both the type of medication and its dosage are correct for their specific needs. Similarly, soldiers in the field, travelers requiring regular injectable medications, and subjects in emergency situations where self-injection is necessary often have difficulty administering the proper dosage of a given drug and often have difficulty in using a conventional syringe. Such problems are also compounded by darkness or poor lighting conditions in battlefield, power failure, and other crisis or emergency situations.

It is well known in the medical injection field that, when administering a drug or other substance intramuscularly, an attempt is made to aspirate blood or other physiological fluid after insertion of the injection needle into a site thought to be suitable. Such an attempted aspiration is made in order to interrogate the injection site (i.e., essentially, as understood in the art the volume of tissue immediately adjacent to and in fluid communication with the open end of the needle) for the presence of blood, lymph, cerebrospinal fluid, or the like. This interrogation is made to insure that pharmaceutical substances or other fluids are not unintentionally injected inappropriately, e.g., into a blood vessel, lymph vessel or into cerebrospinal fluid. The inappropriate administration of a drug or other substance into a blood vessel, lymph vessel or cerebrospinal cavity could result in any of a number of adverse effects including nausea, unwanted toxicity, paralysis, neurological damage or even death. Moreover, the administration of pharmaceutical substances to inappropriate sites often results in attenuation or loss of the substance's desired, specific functional characteristics or activities. Thus, it is of paramount importance to insure that a needle used in administering a drug or other substance be inserted into an appropriate injection site.

For subjects injecting themselves at home, in emergency situations, or in combat, it is virtually impossible to perform the correct procedure. Similarly, personnel who are untrained in medical injection procedures but must give injections because of crisis or emergency situations are much more likely to incorrectly administer a substance, either by administering an incorrect dosage or administering by placing the needle so that its tip is positioned at an inappropriate site (e.g., so that the substance is injected directly into the blood stream rather than intramuscularly).

An example where a pharmaceutical substance must be delivered to an exact site is in the administration of certain chemotherapeutic drugs for the treatment of cancer. It is absolutely necessary that chemotherapeutic drugs be delivered to the exact target tissue. Exposure of some of these drugs to the skin or to the incorrect tissue or to the bloodstream may cause severe side effects. It is thus desirable to have a means for automatically interrogating the fluids in an injection device to insure that blood or other physiological fluids are not being inappropriately aspirated from a possible injection site into the device before drug is administered with the device. Thus, it would also be desirable to have a device which will automatically prevent injection of pharmaceuticals at an undesirable or inappropriate injection site. In other cases, however, it might be desirable or necessary to inject a drug into, for example, the bloodstream; then the interrogation would be to assure that a physiological fluid, such as blood, is aspirated into the injection device before using it to inject the drug.

SUMMARY AND OBJECTS OF THE INVENTION

It is an object of the present invention to provide concealment of an injection needle at all stages of use, thereby reducing the apprehension of the patient.

It is similarly an object of the present invention to maintain sterility of an injection needle at all stages of use by providing means whereby the needle, prior to contact with the skin of a patient for penetration therethrough, is never exposed to any potentially contaminating surfaces, aerosols or airborne particles or microbes.

It is another object of the present invention to provide an injection vial which eliminates the dangers of infection or injury resulting from accidental contact with exposed needles.

It is still another object of the present invention to provide a sanitarily disposable injection vial with a needle which, after use in an injection, retracts completely into said vial to reduce the risk of disease transmission caused by the risk of exposure to a contaminated needle or to a contaminated syringe or to parts thereof.

It is yet another object of the present invention to provide a sanitarily disposable injection vial which can be safely discarded without the need for special equipment or containers and which can be safely and sanitarily disposed of in non-hospital, rugged, or emergency environments.

It is also an object of the present invention to provide an ampule or cartridge for dispensing fluid medication which can be filled by the use of conventional pharmaceutical packaging machinery, thus avoiding the substantial expense which would be required for the development and production of non-conventional packaging methods and machinery.

It is a further object of the present invention to reduce the risk of an improperly administered injection by providing means for precisely, automatically, and programmably controlling the rate of needle insertion, the rate of needle withdrawal, the rate of medicine injection, and the rate of fluid aspiration.

It is also an object of the present invention to reduce the risk that an incorrect dosage of a fluid medicine will be administered by injection.

It is a further object of the invention to reduce the risk that an incorrect drug will be administered to a subject or be self-administered by a subject.

It is an object of the present invention to provide means for the automatic interrogation of an injection site to determine whether or not the injection needle tip is at an appropriate or desired site and in the desired target tissue.

It is a further object of the present invention to provide means for automatically scanning an injection/aspiration cartridge during operation to determine if blood or other physiological fluids have been aspirated from an actual or possible injection site into the cartridge.

It is also an object of the present invention to provide means for automatically preventing the injection of medicines or other fluids into an undesired or inappropriate tissue or site.

Furthermore, it is an object of the present invention to provide means to administer a drug to a pre-selected target tissue and avoid exposure of the drug to tissues which would be undesirably damaged by such exposure.

It is yet another object of the present invention to provide a means for giving or self-administering penile injections of drugs with a minimum of pain and apprehension on the part of the male.

In accordance with the objectives of the invention, a vial for fluid injection is provided. The injection vial is a double-ended cartridge, having a first end and a second end, the cartridge having a cylindrical bore defined by a wall extending between the first end and the second end, the bore being suitable for storing a fluid charge to be expelled therefrom. A first piston and a second piston are positioned within the bore and are slidably seated against the cylindrical wall of the bore, the first piston comprising means for reversibly engaging a plunger. The cartridge is provided with a puncturable end cap which is rigidly attached and sealed to the second end of the cartridge and which comprises a needle guide. The cartridge is also provided with a hollow injection needle having an external tip and an internal tip, the internal tip being rigidly attached to and passing through the second piston, and the external tip extending toward the end cap without protruding therefrom, and means for locking the first piston and the second piston irreversibly together when the first piston and the second piston are a predetermined distance apart. It is preferred that the puncturable end cap be made of a self-sealing material, although this is not necessary for practicing the invention.

The vial may also be provided with a readable indicator to indicate the type of medication, patient information, the amount of medicine to be injected and the various rates of needle insertion and withdrawal and of fluid injection and/or aspiration.

In accordance with another aspect of the invention, a programmable automatic injection/aspiration device is provided having a housing, a chamber disposed within the housing for reversibly receiving a cartridge vial, and a cartridge vial piston operating plunger slidably disposed within the housing. Also provided are means, disposed within the housing, for propelling the plunger. Similarly, controller means for controlling the rate, direction, and extent of movement of the plunger are provided. Control is thus provided via said propelling means, and a programmable processor for directing the controller, a sensor for detecting the rate, direction, and extent of movement of the plunger, an indicator for indicating the rate, direction, and extent of movement of the plunger and for indicating the amount of fluid remaining and expelled from a fluid vial, and a sensor for detecting the presence in the vial of aspirated physiological fluids are also provided. Similarly provided are means for automatically preventing injection into an undesirable target tissue upon the detection of aspirated physiological fluid, and locking means for preventing unintentional discharge of drug from a cartridge vial disposed in the injection/aspiration device.

In accordance with the invention a cartridge vial, containing a fluid medicine charge, may be inserted into an injection/aspiration device, which may then be used to administer the medicine by injection. Finally, the cartridge vial, with completely retracted needle, may be removed and discarded, while the injection/aspiration device may be repeatedly re-used with different cartridge vials.

BRIEF DESCRIPTION OF THE DRAWINGS

The invention will now be described with reference to the enclosed drawings, in which.

DETAILED DESCRIPTION OF THE PREFERRED EMBODIMENTS

The injection/aspiration device, illustrated in FIG. 1, comprises: a housing 201 for disposition of the various components having a chamber 219 for reversibly receiving a cartridge vial of a type as described below and in FIGS. 2 and 3, a d.c. motor 203, a lead screw 205, a linear bearing 207 for holding a lead nut, a lead nut 213 surrounding the lead screw, and armed/safety injector switch 209, indicating light emitting diodes 211, a plunger 215 attached to lead screw 205, a cartridge vial 217 disposed within chamber 219, an electronic control unit 221, an injector trigger button 223, a d.c. power source 225, an on/off switch 227, a cartridge/ampule position locking solenoid 229 having cartridge/ampule position locking solenoid shaft 231, aspirated fluid sensor 233, and plunger shaft rate/position/direction sensor 235.

The injection/aspiration device of the invention operates in conjunction with cartridge vials as described hereinbelow. All of the components of the device are energized by d.c. power source 225 through the operation of switch 227. D.c. motor 203 propels lead screw 205 which is attached to lead nut 213 and plunger shaft 215 which is reversibly attached to cartridge vial shaft end 216 by means of a mechanical key way provided at the end of plunger shaft 215. Linear bearing 207 is provided for smooth operation of lead screw 205 and plunger shaft 215. Lead screw nut 213 is provided as an attachment means for connecting lead screw 205 to plunger shaft 215. Electronic control unit 221 is a programmable electronic processor connected by means of wires not shown to d.c. motor 203 to control the rate, direction, and extent of movement of lead screw 205, plunger shaft 215 and, thereby, the rate, extent of movement, and direction of movement of cartridge vial shaft end 216. Cartridge vial shaft end 216 can be of any type configured to securely but reversibly attach to plunger shaft 215.

Similarly, as described below, plunger shaft 215 can be adapted to operate other types of cartridge vials such as those designed to be used with a spear type shaft of a type known in the dental cartridge field. The electronic control unit 221 is programmed by means of a programmable read-only memory (PROM), and a programmable array logic (PAL) which, depending on the application of the device, can be interchanged to adapt the device to the age or sex of the patient, the location parameters of the injection, (such as intramuscular, subcutaneous or intravenous) for the rate of needle withdrawal and insertion, and for the rate of medicinal charge injection. The electronic control unit also comprises electronic timers which control the overall timing and specific rates during the injection process. A set of programmed instructions are stored in a replaceable and interchangeable memory chip (not shown) in electronic control unit 221. By either interchanging memory chips or by reprogramming programmable memory chips, the various functions of the injection/aspiration device can be controllably varied. Cartridge/ampule position locking mechanism 229 is a solenoid which can be activated to lock a cartridge vial in a particular position by means of cartridge/ampule position locking solenoid shaft 231 so that blood or other fluids can be aspirated. Although a solenoid and solenoid shaft are described herein as a locking mechanism, it can be clearly seen that many other means for accomplishing the objective of the device to lock any type of cartridge vial in a particular position in the injection/aspiration device housing can be used.

Similarly, although programmable and/or interchangeable memory chips are described examples herein, it can be clearly seen that many other means for programming the stated functions could be used to accomplish the objectives of the invention.

It is also clear that although a d.c. motor and power source and electronic components are described herein as means for controlling the various rates of operation of the various components of the invention that other means such as compressed gas and valves could also be used.

Figure 1:
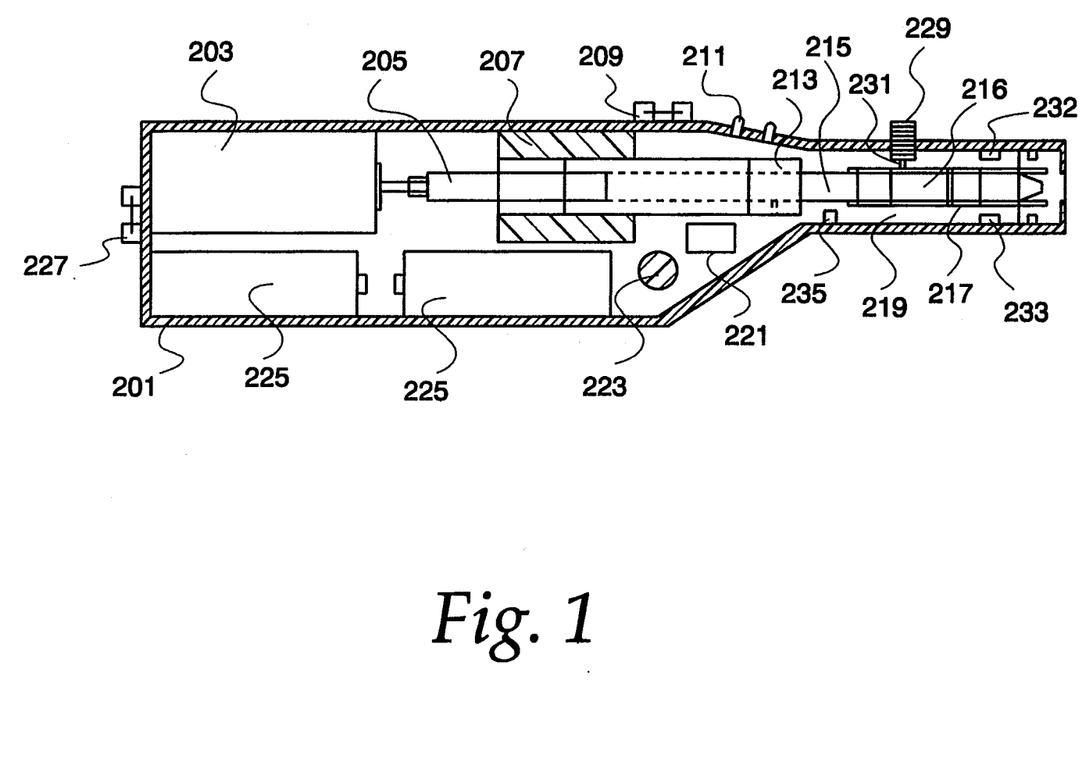
FIG. 1 is a longitudinal cross-sectional view of an injection/aspiration device showing the relative placement of the cartridge vial and other components.

Although not shown in FIG. 1, the various electronic and electrical components of the invention are connected by electrical circuitry.

It should also be clear that many different means for securely connecting to and easily disengaging a cartridge vial to and from plunger shaft 215 are possible. As an example and not described as a limitation, FIG. 3 shows plunger shaft 47 of an injection/aspiration device having pointed barbed plunger shaft head 49 similar to pointed shafts known in the dental injection cartridge field which is driven a sufficient distance into piston 45 during operation of the invention that a sufficiently secure connection is made to operate piston 45 in both directions. Disconnection of barbed head 49 from piston 45 is achieved by the retraction of plunger shaft 47 and plunger shaft head 49 a sufficient distance into lead nut 213 which is of an appropriate internal diameter to accomplish the disconnection.

The cartridge vial portion of the invention includes a hollow injection/aspiration needle attached to one piston with its external pointed end initially disposed within a sealed end cap for sanitary purposes. A second piston is also provided in the cylindrical bore to operate in conjunction with the first piston to impel the injection needle and the injection fluid into the subject and then withdraw the injection needle and first piston from the subject through the sealed end cap sufficiently so that the point of the needle need not be exposed to the atmosphere before, during, or after operation of the invention. The present invention provides a means for withdrawing the needle tip into a disposable cartridge immediately after the injection and before the injector device is withdrawn from contact with the subject. This reduces the risk of unintentional exposure to a used needle tip by both users and non-users because the needle tip need never be exposed.

The programmable automatic injector portion of the invention includes a chamber for insertion of a vial, a piston operating plunger for operation of the vial, and a power source for operating the plunger.

Cartridge Vial Embodiments

The advantages and characteristics of the cartridge vial and injection/aspiration device according to the present invention can be elucidated from the following detailed description of one embodiment of the injection/aspiration device and three embodiments of the cartridge vial, to be taken as examples and not as limitations in conjunction with the accompanying drawings.

Figure 3:
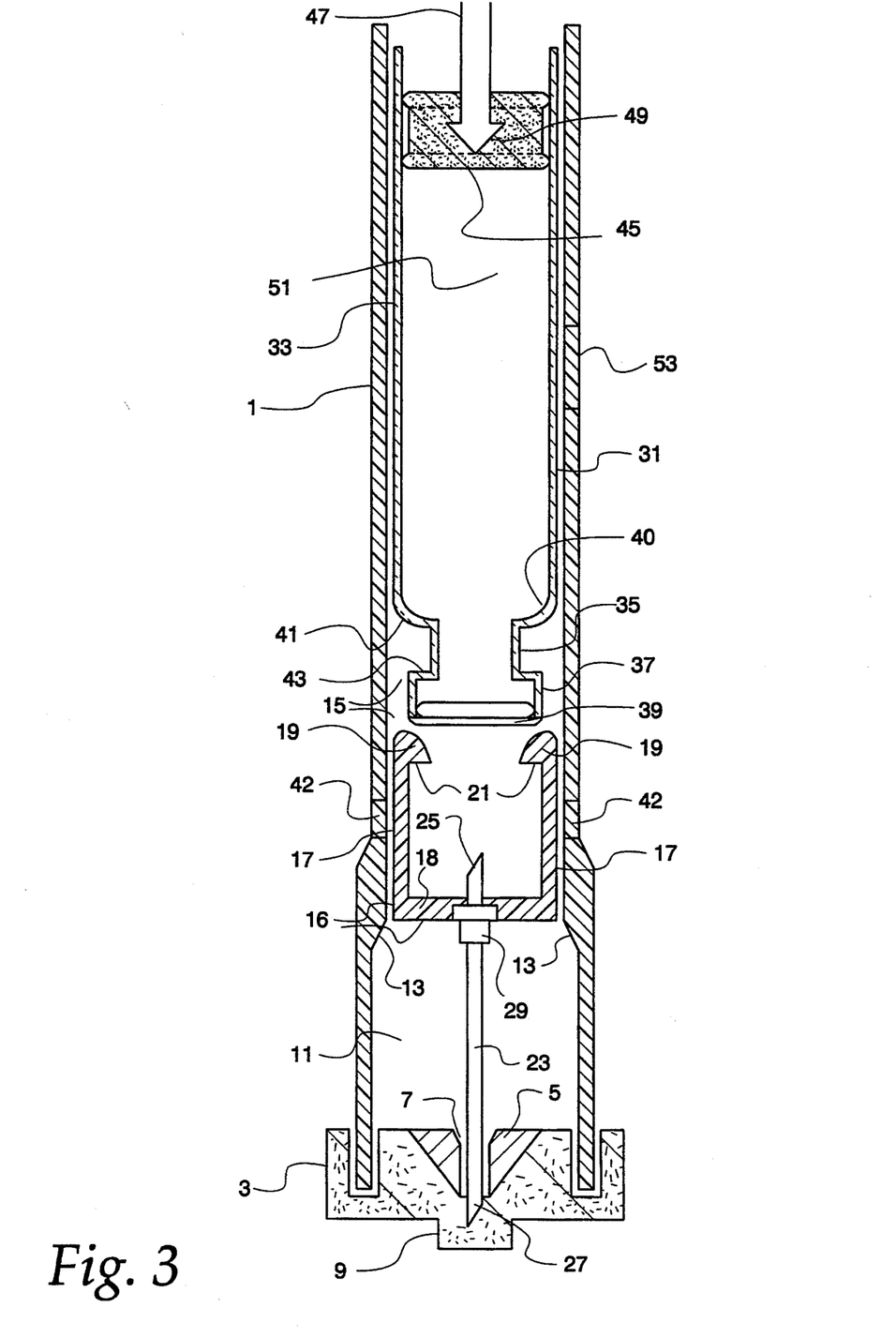
FIG. 3 illustrates another embodiment of the cartridge vial.

With reference to FIG. 3, a cartridge vial comprises a double-ended circularly cylindrical housing 1 constructed of rigid material and having a cartridge/ampule position locking solenoid shaft aperture 53, aspirated fluid sensor apertures 42 an ampule residence chamber 15 and cylindrical needle housing assembly receiving chamber 11. Cartridge housing 1 is provided with a puncturable sealing end cap 3 of resilient material, a plastic needle guide 5 rigidly embedded in the end cap 3 and having needle guide aperture 7 formed therein and an injection device positioning projection 9. The needle assembly receiving chamber 11 is further provided with curved abutments 13 of appropriate configuration to allow the needle assembly housing 16 to both enter and withdraw from needle assembly housing receiving chamber 11. Needle assembly housing 16 and ampule 31 are both initially disposed within ampule residence chamber 15. A glass ampule 31, positioned within the cartridge, is provided with a three portion chamber in which is stored a fluid charge 51. The first portion 33 of ampule 31 freely communicates with second portion 35 and third portion 37. Third portion 37 is provided with a puncturable ampule stopper 39 of a resilient material. An ampule piston chamber abutment 40 forms the transition between first ampule portion 33 and second ampule portion 35 and forms a stop for a piston 45 during operation of the invention. The external portion of the transition between first ampule portion 33 and second ampule portion 35 forms an ampule shoulder 41. Ampule 31 is further provided with flange engaging lips 43 which are formed by the narrowing transition area between second chamber portion 35 and third chamber portion 37.

Ampule 31 is further provided with a piston 45 of resilient material for reversibly engaging a pointed plunger shaft head 49 having a plunger shaft 47 of an injection/aspiration device. Such an ampule could be reversibly engaged to the injection/aspiration device by many other means, other than a piston like piston 45 as shown, such as a T-shaft and keyway or any other means providing secure reversible engagement of a cartridge device to an injection/aspiration device.

Needle assembly housing 16 is provided with a needle assembly housing bottom 18, needle housing walls 17, needle assembly housing flanges 19 and needle assembly housing lips 21 disposed for securely engaging ampule 31. Needle assembly housing 16 is further provided with a hollow injection needle 23 which is supported by a collar 29 and passes therethrough and has an internal tip 25 disposed toward puncturable ampule stopper 39 and an external tip 27 which passes through aperture 7 of needle guide 5 but does not protrude through sealing end cap 3.

Needle assembly housing walls 17 are of sufficient length so that, in operation of the cartridge as described hereinbelow, third ampule portion 37 is captured by the engagement of needle assembly housing flange lips 21 by flange engaging lip 43 of ampule 31 before needle internal end 25 contacts puncturable ampule end stopper 39 and when ampule 31 has been propelled a sufficient distance toward puncturable cartridge sealing end cap 3 that needle assembly housing 16 is fully within needle assembly housing receiving chamber 11.

Although a bar code indicator is seen as an efficient means for labeling both the cartridge vial and injector/aspirator components of the invention, any other means or multiple means could be employed to label the invention for machine readable purposes and for human readable purposes. For instance, both components of the invention could be labeled concurrently with readable magnetic strips, braille bumps and alphanumeric symbols.

The above-described embodiment of the ampule type cartridge vial of the invention operates as described hereinbelow.

Piston 45 is propelled toward sealable end cap 3 by the application of force to plunger shaft 47 which force is communicated through plunger shaft head 49 to piston 45 thus applying hydraulic pressure through fluid charge 51 and forcing ampule 31 onto needle assembly 16. Continued pressure on plunger shaft head 47 is communicated through needle housing flanges 19 needle housing walls 17 and needle housing bottom 16 to needle 23, thus propelling needle 23 through needle guide aperture 7 causing external needle tip 27 to puncture puncturable end cap 3. Continued force toward puncturable cartridge sealing end cap 3 by piston 45 continues to propel needle 23 outward until needle housing 16 is stopped by sealable end cap 3, thus positioning needle assembly housing 16 within needle assembly receiving chamber 11 which is of a larger diameter than ampule residence chamber 15. The positioning of needle assembly housing 16 within the needle assembly receiving chamber allows flanges 19 and walls 17 of needle assembly housing 16 to expand to irreversibly and securely receive and capture the third portion 37 of ampule 31. Continued pressure in the same direction causes puncturable ampule stopper 39 on ampule 31 to be driven into internal needle tip 25 thus puncturing ampule stopper 39 and causing ampule stopper 39 to contact needle assembly housing bottom 18. At this time in the operation of the invention, cartridge/ampule position locking solenoid 229 (shown in FIG. 1 but not shown in FIG. 3) is energized causing cartridge/ampule position locking solenoid shaft 231 (also shown in FIG. 1 but not shown in FIG. 3) to extend through cartridge/ampule position locking solenoid aperture 53 thus locking ampule 31 and needle assembly housing 16 tightly against needle guide 5.

The direction of force on plunger shaft head 49 may then be reversed causing a slight withdrawal of piston 45 away from end cap 3, thus causing aspiration into fluid 51 in ampule 31 of physiological fluid(s) if needle tip 27, now located at a possible injection site in tissue, is in communication with such fluid. An aspirated fluid sensor 233 and light source, such as a photodiode or photocell 232 in the injection/aspiration component of the invention (shown in FIG. 1 but not in FIG. 3), then scan the fluid in ampule 31 through aspirated fluid sensor apertures 42 to spectrophotometrically detect the presence of physiological fluid(s).

If no fluids are detected and it is regarded as desirable or appropriate that none be aspiratable from an injection site for the drug being administered, or if fluid(s) that are detected do not indicate that the possible injection site, at which needle tip 27 is located is undesirable or inappropriate, the injection cycle continues and the site at which needle tip 27 is located, is employed as the injection site. Continued force in the same direction toward end cap 3 on piston 45 causes the expulsion of fluid charge 51 through needle 23 into the subject. In operation of the invention, with respect to an automatic injection/aspiration device of the type discussed above, the rate of propulsion of piston shaft head 49 is varied to control the rate of insertion of needle 23 and the rate of injection of fluid charge 51. Also in the operation of the invention, a typical time for this sequence of inserting hollow injection needle 23 is on the order of 100 milliseconds. After the injection of fluid charge 51 the operational sequence is continued into the retraction/needle capture stage by the reversal of force on piston shaft head 49 thus causing pressure on piston 45 to be directed away from sealing cap 3. The partial vacuum created by the withdrawal of piston 45 causes ampule 31 to retract from needle 23 a sufficient distance so that internal needle tip 25 no longer penetrates puncturable ampule end stopper 39. The retraction of ampule 31 from needle tip 25 is assisted by the biasing force caused by the contact between curved needle assembly housing flanges 19 and curved ampule lips 21 are then engaged to flange engaging lips 43 on ampule 31. Locking solenoid shaft 231 (shown in FIG. 1 but not in FIG. 3) is then withdrawn allowing further retention of the connected ampule/needle assembly. The ampule and needle assembly, thus irreversibly engaged, is withdrawn as piston 45 is withdrawn by continued force in the direction away from puncturable sealing end cap 3 thus withdrawing needle 23 from the injection site a sufficient distance so that external needle tip 27 is captured completely within needle assembly receiving chamber 11. Thus, no part of needle 23 need ever be exposed to any environment other than the subject's tissues or the inside of the cartridge vial. A typical time for operation of the withdrawal/needle capture sequence is on the order of 200 milliseconds.

During operation of the invention, if an undesirable or inappropriate physiological fluid (e.g. blood) or lack of physiological fluid (e.g., lack of blood if an intravenous injection is intended) is detected by aspirated fluid sensor 233, the injection sequence may be automatically stopped, thus preventing the injection of medicine or other fluids into an undesirable or inappropriate injection site.

Figure 4:
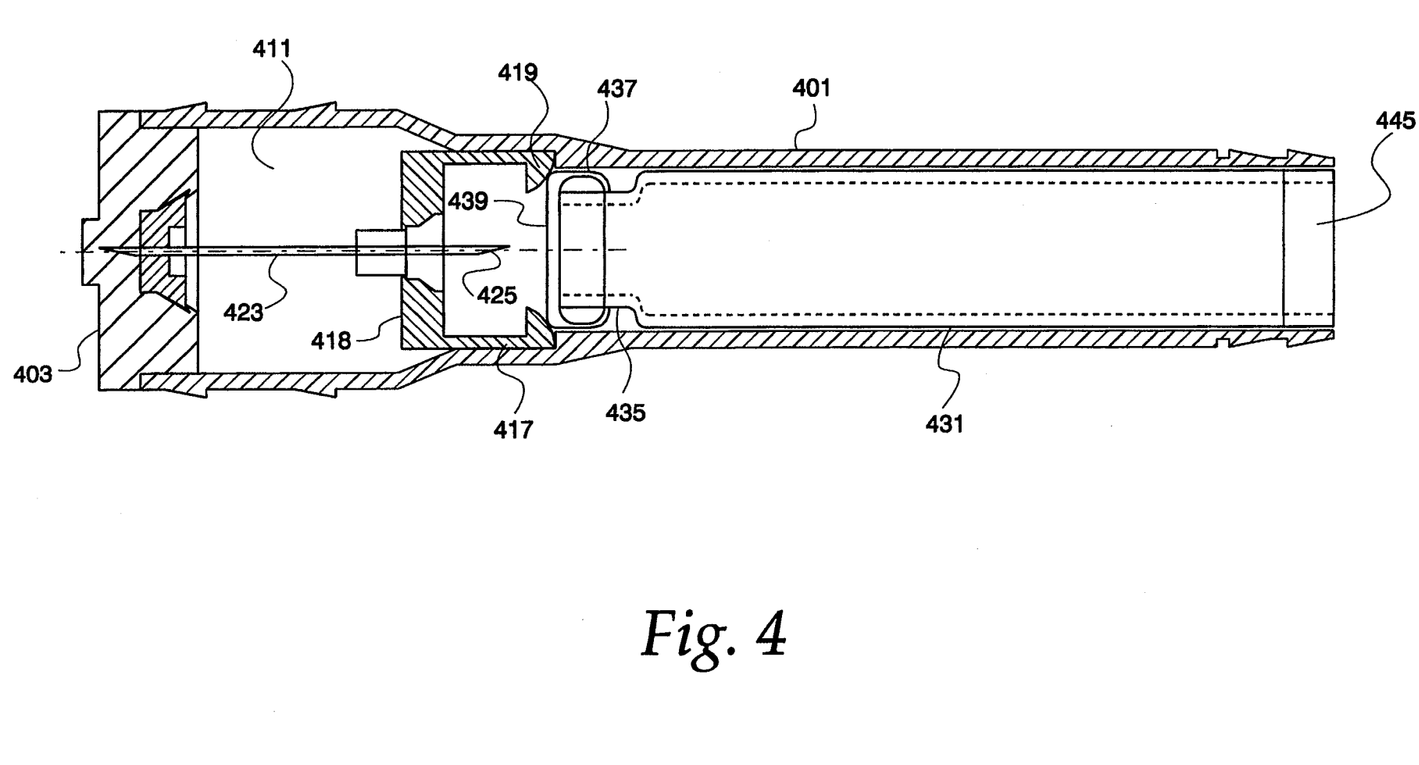
FIG. 4 illustrates an additional embodiment of the cartridge vial similar to that shown in FIG. 3 but for injections only and wherein certain dimensional relationships are varied.

With reference to FIG. 4, an embodiment of the cartridge vial of the present invention intended for injections where no aspiration is necessary is illustrated. Cartridge 401 is provided with a needle assembly receiving chamber 411 enclosed with a puncturable end cap 403 sealing the cartridge 401. Disposed within the cartridge 401 is a slidable ampule 431 having piston 445 for the receipt of a barbed plunger shaft head known in the dental injection cartridge field and having a second ampule portion 435 which is smaller than third ampule portion 437 the transition area therebetween forming an engaging surface for engaging flanges 419 of needle housing assembly 418. Needle assembly housing 418 is provided with needle assembly housing walls 417 of sufficient length that when the flanges capture third portion 437 of ampule 431 needle tip 425 has already punctured puncturable ampule end stopper 439. It can thus clearly be seen that the retraction of needle assembly housing 418 and needle 423 are accomplished without permitting the withdrawal of needle tip 425 from puncturable end cap 439.

The additional advantages and characteristics of a non-ampule type embodiment according to the present invention can also be elucidated from the following detailed description of a second embodiment of the cartridge vial component, to be taken as an example and not as a limitation in conjunction with the accompanying drawings.

Figure 2:
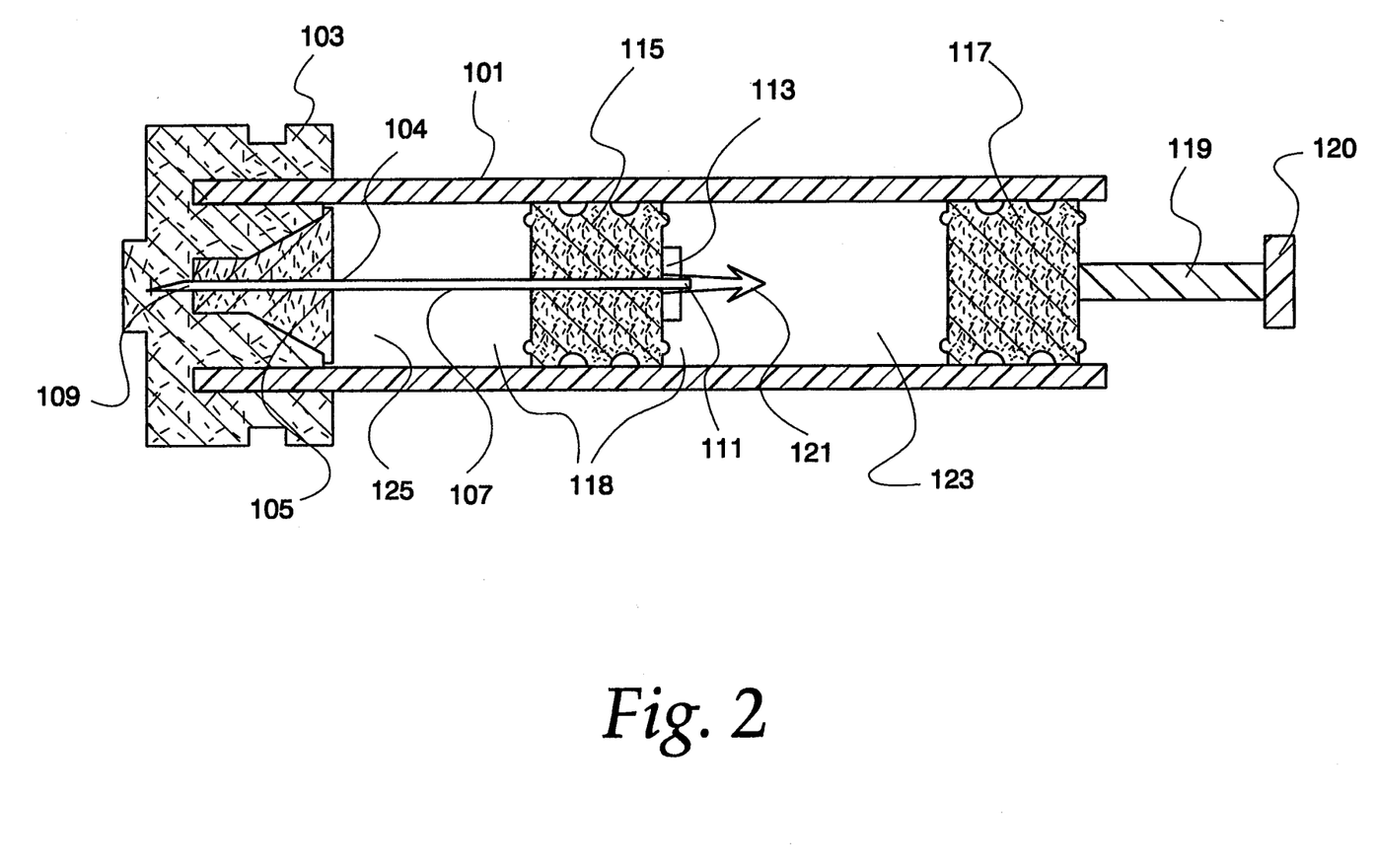
FIG. 2 is a longitudinal cross-sectional view of the cartridge vial constructed in accordance with a first embodiment of the invention.

The cartridge type vial illustrated in FIG. 2 comprises: a double-ended circularly cylindrical glass tube 101 provided with a puncturable sealing end cap 103 of resilient material, a rigid plastic needle guide 105 rigidly embedded in the puncturable end cap, and a first piston 117 slidably seated within the bore 118 of the cartridge. First piston 117 is provided with an operating rod engagement shaft 119 having shaft head 120. The cartridge also comprises a second piston 115 which is also slidably disposed within the bore 118 of the cartridge. An internal end 111 of hollow injection needle 107 passing through piston 115 and is rigidly attached thereto by a needle anchoring washer 113. Hollow injection needle 107 also has an external end 109 which extends through a cylindrical aperture 104 in needle guide 105 so that tip 109 at the external end does not pass through puncturable end cap 103. Cylindrical aperture 104 is of sufficient diameter to allow the expulsion of air from chamber 125 during operation of the device. Second piston 115 is also rigidly fitted with a stainless steel engaging barb 121 which extends toward first piston 117. Medicinal fluid charge 123 is disposed between piston 117 and piston 115.

The cartridge vial of the invention operates as described hereinbelow.

The space in bore 118 between piston 117 and piston 115 is filled with a charge of fluid medicine 123 to be injected into a subject. Piston 117 is propelled by means of a rigidly connected piston rod 119 toward piston 115 forcing piston 117 toward piston 115 thus applying hydraulic pressure through fluid charge 123 to piston 115 which forces piston 115 longitudinally through the bore 118 of the cartridge. This in turn drives hollow injection needle 107 which is guided by needle guide 105 through puncturable end cap 103. Continued pressure on piston shaft head 120 communicated through piston shaft 119 drives piston 115 onto needle guide 105 which stops piston 115. Cartridge/ampule position locking solenoid 229 (not shown in FIG. 2, see FIG. 1) is then operated to insert solenoid shaft 231 (not shown in FIG. 2, see FIG. 1) thus locking cylinder 101 against end cap 103.

The direction of force on piston plunger shaft head 120 may then be reversed to cause a slight withdrawal of piston 117 away from end cap 103 thus causing aspiration of physiological fluid(s), into fluid charge 123, if needle tip 109, now located at a possible injection site in tissue, is in communication with such fluid. Aspirated fluid sensor 233 and light source (photodiode or photocell 232) (shown in FIG. 1 but not in FIG. 2) in the injection/aspiration component of the invention (shown in FIG. 2 but not in FIG. 1) then scans the fluid in the bore between piston 117 and piston 115 to detect the presence of physiological fluid(s). If no fluids are detected and it is regarded as desirable or appropriate that none be aspiratable at the possible injection site at which needle tip 109 is located, or if the fluid(s) that are detected do not indicate that the possible injection site is undesirable or inappropriate, the injection cycle continues.

Continued force on piston 117 through piston shaft 119 then causes expulsion of the medicinal fluid charge 123 through hollow injection needle 107 and into the subject. Continued force on piston shaft 119 impels piston 117 to be within a predetermined distance from piston 115 sufficiently onto barb 121 to irreversibly lock needle 107 and piston 117 to piston 115 as a last portion of medicinal fluid charge 123 is expelled from the bore. Locking solenoid shaft 231 (not shown in FIG. 2, see FIG. 1) is then withdrawn allowing withdrawal of the cartridge. When the direction of the force on piston shaft 119 is reversed, piston 117 withdraws away from end cap 103 through the cartridge bore drawing piston 115 which has been locked to piston 117 by means of stainless steel locking barb 121 away from needle guide 104 thus withdrawing needle 107 which is rigidly attached by anchor washer 113 to piston 115. Continued force in this withdrawal direction on piston shaft 119 withdraws point 109 of needle 107 through puncturable end cap 103 and needle guide 105 so that needle end 109 is captured within the cylindrical bore of the cartridge, thus the entirety of needle 107 is disposed completely within bore 118 of the cartridge after the injection cycle is completed.

During operation of this embodiment, if an undesirable or inappropriate physiological fluid (e.g. blood) or lack of physiological fluid (e.g., lack of blood if an intravenous injection is intended) is detected by aspirated fluid sensor 233 the injection sequence is automatically stopped, thus preventing the injection of medicine or other fluids into an undesirable or inappropriate injection site.

Although a preferred method of using the cartridge vials of the types described above is with a powered automatic injection/aspiration device also as described above, it can be clearly seen that a manually powered injection device could be configured to operate such cartridge vials.

With reference to the resilient materials disclosed herein, such materials are those standard in the medical and dental packaging and hypodermic syringe art such as rubber, plastics, and other synthetic and non-synthetic materials known in the art for accomplishing similar and related objectives. Also, all of the embodiments of the cartridge vials disclosed herein are adapted to be manufactured by standard medical and dental ampule and container manufacturing equipment.

Similarly, the cartridge vials disclosed herein are adapted to contain, when fully charged, from 0.1 to 100 milliliters of fluid. However, more typically such vials will contain, when fully charged, from 0.5 to 10 milliliters of fluid.

The needles will have lengths and gauges, and will be made of materials, that are standard in the hypodermic syringe/needle art.

What is claimed is:

1. A fluid injector actuated by a plunger, said fluid injector comprising:
(A) a tubular cartridge having an upper end and a lower end, said cartridge having an interior bore wall which widens at said lower end of said cartridge to form a needle housing assembly residence chamber for receiving a needle housing assembly;
(B) a puncturable end cap sealing said lower end of said cartridge;
(C) an ampule slidably disposed within the upper end of said cartridge bore wall, said ampule having an upper end and a lower end and being suitable for storing a fluid charge to be expelled therefrom;
(D) a piston slidably seated within said ampule and engageable by said plunger from said upper end of said ampule;
(E) a puncturable ampule end stopper rigidly attached to and sealing said lower end of said ampule; and
(F) a needle housing assembly slidably disposed within said upper end of said cartridge below said ampule, said needle housing assembly comprising:
a housing having a housing bottom and flexible upstanding housing walls attached to the periphery of said housing bottom, said housing walls extending toward said lower end of said ampule and having upper edges thereon,
a hollow injection needle extending through and rigidly engaged by said housing bottom and having an internal section, and an external section, said internal section of said hollow injection needle extending from said housing bottom, upwardly within said housing walls, toward said puncturable ampule end stopper, and said external section of said hollow injection needle extending from said housing bottom downwardly toward said puncturable end cap of said cartridge, said needle being within said cartridge between said puncturable ampule end stopper and said puncturable end cap, the upper edges of said housing walls being engageable with said lower end of said ampule as said ampule slides downwardly within said cartridge bore, whereby actuation by said plunger moves said ampule downwardly within said interior bore wall in said upper end of said cartridge toward said lower end of said cartridge thus engaging said upper edges of said housing walls and moving said needle housing assembly from said upper end of said cartridge into said needle housing assembly residence chamber at said lower end of said cartridge causing said external section of said hollow injection needle to protrude through said puncturable end cap and allowing said flexible housing walls to expand outwardly in said needle housing assembly residence chamber, the further downward movement of said ampule causing the internal section of said hollow injection needle to pass through said puncturable ampule end stopper thereby allowing fluid to be injected outwardly through said hollow injection needle.

2. A fluid injector in accordance with claim 1 wherein said ampule further comprises a first cylindrical portion, a second cylindrical portion adjacent to and narrower than said first portion, and a third cylindrical portion adjacent to and wider than said second portion.

3. A fluid injector in accordance with claim 2 wherein said upper ends of said housing walls engageable with said ampule further comprises locking means for irreversibly locking said needle housing assembly to said ampule at said third cylindrical portion of said ampule when said needle housing assembly and said ampule are engaged.

4. A fluid injector in accordance with claim 3 wherein said housing walls further comprise needle assembly housing lips at said upper edges of said housing walls, said lips engageable with said ampule.

5. A fluid injector in accordance with claim 1 wherein said interior bore wall is cylindrical.

6. A fluid injector in accordance with claim 1 further comprising a needle guide disposed in said puncturable end cap.

7. A fluid injector in accordance with claim 1 wherein said ampule has a circumferential recess or groove located adjacent its lower end and wherein the upper edges of said housing walls have inwardly extending sections for engaging the lower end of said ampule.

8. A fluid injector in accordance with claim 1 wherein said piston further comprises means for reversibly engaging said plunger.

9. A fluid injector in accordance with claim 1 wherein said upper end of said tubular cartridge receives an assembly which comprises a spring for engaging said plunger for actuation to move said ampule within said interior bore wall.

10. A fluid injector in accordance with claim 1 wherein said external section of said hollow injection needle is retractable from said puncturable end cap with the retraction of said needle housing assembly within said cartridge.

11. A fluid injector in accordance with claim 1 wherein said ampule moves downwardly within said housing of said needle housing assembly causing the internal section of said hollow injection needle to pass through said puncturable ampule end stopper.

12. An injector positionable on external tissue for delivering fluid into a preselected internal target tissue while avoiding fluid exposure to the surface tissue comprising:

a tubular cartridge, having a first end and a second end, said cartridge having an interior bore wall which is widened at said second end of said cartridge;

a hollow injection needle positioned axially within said tubular cartridge, said hollow injection needle having an inwardly positioned end directed toward said upper end of said tubular cartridge and an external end directed toward said lower end of said tubular cartridge;

a housing supporting said hollow injection needle positioned axially within said tubular cartridge, said housing being slidable in said tubular cartridge and having expandable walls along side said inwardly positioned end of said hollow injection needle;

an ampule containing said fluid positioned in said tubular cartridge above said hollow injection needle, said ampule having a puncturable end stopper facing the inwardly positioned end of said hollow injection needle;

means for propelling said housing supporting said hollow injection needle together with said ampule within said tubular cartridge causing said external end of said needle to puncture the surface tissue and extend outward from said cartridge through the surface tissue into the target tissue;

means for further propelling said ampule within said cartridge in the direction of said hollow injection needle causing the walls of said housing to expand in the widened lower end of said tubular cartridge and said puncturable end stopper on said ampule to be punctured by said inwardly positioned end of said hollow injection needle allowing said inwardly end to extend into said ampule; and means for expelling said fluid from said ampule through said external end of said hollow injection needle into said internal target tissue.

13. An injector in accordance with claim 12 further comprising means for retracting said housing supporting said hollow injection needle within said tubular cartridge causing said external end of said needle to retract from the surface tissue and into said cartridge.

14. A fluid injector comprising:

(A) a tubular cartridge, having a first end and a second end, said cartridge having an interior bore wall which is widened at said second end of said cartridge to form a needle housing assembly residence chamber for reversibly receiving a needle housing assembly, and a puncturable end cap, said end cap sealing said second end of said cartridge and having a needle guide disposed therein;

(B) an ampule disposed within said interior bore wall, said ampule having a first elongated cylindrical portion, a second cylindrical portion adjacent to and narrower than said first portion, and a third cylindrical portion adjacent to and wider than said second portion, said ampule being suitable for storing a fluid charge to be expelled therefrom;

(C) a piston slidably seated within said first portion of said ampule;

(D) a plunger engageable with said piston for exerting a force against said piston;

(E) a puncturable ampule end stopper rigidly attached to and sealing said third portion of said ampule; and (F) a needle housing assembly disposed in said interior bore of said cartridge said needle housing assembly comprising:

a housing, a hollow injection needle rigidly attached to said housing and having an internal end and an external end, said internal end of said needle extending through said needle housing assembly toward said puncturable ampule end stopper, and said external end of said hollow injection needle extending toward said puncturable end cap of said cartridge, said needle being within said cartridge between said puncturable ampule end stopper and said puncturable end cap, said housing having locking means for irreversibly locking said needle housing assembly to said ampule when said needle housing assembly and said ampule are brought together upon said plunger exerting a force against said piston moving said ampule and said housing toward said second end of said cartridge wherein the locking means of said housing expand outwardly in the widened interior bore wall of said second end to lock said housing with said ampule.

* * * * *